US010869750B2

(12) United States Patent
Greiner et al.

(10) Patent No.: US 10,869,750 B2
(45) Date of Patent: Dec. 22, 2020

(54) ENDOVASCULAR STENT GRAFTS AND METHODS OF USING SAID STENT GRAFTS

(71) Applicant: Rheinisch-Westfälische Technische Hochschule (RWTH) Aachen, Aachen (DE)

(72) Inventors: Andreas Greiner, Berlin (DE); Stefan Jockenhövel, Aachen (DE); Andrij Pich, Aachen (DE); Larissa Hussmann, Cologne (DE); Valentine Gesché, Aachen (DE)

(73) Assignee: Rheinisch-Westfälische Technische Hochschule (RWTH) Aachen, Aachen (DE)

( * ) Notice: Subject to any disclaimer, the term of this patent is extended or adjusted under 35 U.S.C. 154(b) by 163 days.

(21) Appl. No.: 16/126,246

(22) Filed: Sep. 10, 2018

(65) Prior Publication Data
US 2020/0078161 A1 Mar. 12, 2020

(51) Int. Cl.
| | |
|---|---|
| *A61F 2/07* | (2013.01) |
| *A61L 31/14* | (2006.01) |
| *A61L 31/16* | (2006.01) |
| *A61L 31/04* | (2006.01) |
| *A61B 17/11* | (2006.01) |
| *A61F 2/86* | (2013.01) |
| *A61F 2/90* | (2013.01) |
| *A61F 2/91* | (2013.01) |

(52) U.S. Cl.
CPC ............... *A61F 2/07* (2013.01); *A61B 17/11* (2013.01); *A61L 31/048* (2013.01); *A61L 31/145* (2013.01); *A61L 31/146* (2013.01); *A61L 31/16* (2013.01); *A61B 2017/1107* (2013.01); *A61F 2/86* (2013.01); *A61F 2/90* (2013.01); *A61F 2/91* (2013.01); *A61F 2002/077* (2013.01); *A61F 2210/0076* (2013.01); *A61F 2250/0067* (2013.01); *A61L 2300/414* (2013.01); *A61L 2300/426* (2013.01)

(58) Field of Classification Search
CPC ...... A61F 2/07; A61F 2/89; A61F 2/90; A61F 2/91; A61F 2/915; A61F 2210/0061; A61L 31/145
See application file for complete search history.

(56) References Cited

U.S. PATENT DOCUMENTS

| | | | | |
|---|---|---|---|---|
| 2007/0078480 | A1* | 4/2007 | Belenkaya | ............ A61L 31/145 606/200 |
| 2012/0089218 | A1* | 4/2012 | Dardi | ...................... A61F 2/844 623/1.15 |
| 2015/0122687 | A1* | 5/2015 | Zeng | ..................... A61F 2/2412 206/438 |

OTHER PUBLICATIONS

Loewen, Alexander, et al., PowerPoint Presentation Entitled "Development of a Controlled-Occluding Membrane as a Stent Graft Component for Spinal Cord Ischaemia Prophylaxis", Jahrestagung der Biomedizinischen Technik, Institut für Textiltechnik of RWTH Aachen University, Dresden, Sep. 12, 2017, pp. 1-21.

* cited by examiner

*Primary Examiner* — Suba Ganesan
(74) *Attorney, Agent, or Firm* — McDonnell Boehnen Hulbert & Berghoff LLP

(57) ABSTRACT

AN endovascular stent graft including a hydrogel capable of retarded swelling when coming into contact with blood upon implantation in a patient is provided. Methods for the treatment of aneurysms and the prevention of ischemic neurological damage, in particular spinal cord damage, in patients receiving aneurysm repair procedures, using said endovascular stent grafts is also provided.

23 Claims, 12 Drawing Sheets

US 10,869,750 B2

ENDOVASCULAR STENT GRAFTS AND METHODS OF USING SAID STENT GRAFTS

FIELD OF THE INVENTION

The present invention relates to endovascular stent grafts comprising a hydrogel capable of retarded swelling when coming into contact with blood upon implantation in a patient, and methods for the treatment of aneurysms and the prevention of ischemic neurological damage, in particular spinal cord damage, in patients receiving aneurysm repair procedures, using said endovascular stent grafts.

BACKGROUND OF THE INVENTION

Thoracic and thoracoabdominal aortic aneurysms (TAAA) are complex and life-threatening diseases that can affect not only elderly but also younger patients. Open aneurysm repair is a possible surgical intervention in this respect that is, however, potentially associated with high morbidity and mortality.

The risks and complications associated with surgical aneurysm repair have been reduced by implementation of endovascular approaches using stent grafts that are implanted in the affected aortic regions. However, the risk of ischemic neurological damage, in particular spinal cord ischaemia that can lead to paraplegia, resulting from the occlusion of the blood supply to the spinal cord by intercostal and lumbar collateral arteries (FIG. 1), is an unsolved problem of endovascular TAAA repair.

In contrast to open surgery, there is no possibility to create intraoperative bypasses for the blood supply to the spinal cord in endovascular TAAA repair. Attempts to solve this problem by the use of fenestrated stent grafts, branched stent grafts or chimney grafts have been made. Further, multi-stage endovascular surgery approaches using branched stent grafts that are initially left partially open and then closed in a later procedure have been attempted. However, recent studies still report paraplegization rates of almost 30% for endovascular TAAA repair. Moreover, multi-stage procedures place high stress and increased risk on the patient.

Thus, regarding the complex and unpredictable blood supply to the spinal cord by intercostal and lumbar collateral arteries, there is as of yet no adequate solution for maintaining said blood supply in TAAA repair using endovascular stent grafts.

Therefore, a strong need exists to provide means for a controlled and delayed occlusion of intercostal and lumbar collateral arteries in endovascular TAAA repair, allowing for the formation of essential collateral spinal cord blood supply during said occlusion.

This need is satisfied by providing the embodiments characterized in the claims.

SUMMARY OF THE INVENTION

The present invention relates to an endovascular stent graft comprising an area having one or more through holes coated at least partially with a hydrogel capable of retarded reduction of the diameter of or retarded occlusion of said through holes by swelling upon implantation in a subject.

Further, the present invention relates to methods for the repair of an aneurysm in a subject, comprising the step of implanting said endovascular stent graft of the present invention into the affected vascular region of the subject.

Moreover, the present invention relates to methods for the prevention of ischemic neurological damage in a subject that is to receive an endovascular stent graft for the treatment of an aneurysm, comprising the step of implanting said endovascular stent graft of the present invention into the affected vascular region of the subject to treat said aneurysm.

Finally, the present invention relates to tubular shunts, wherein the inner walls of said shunts are coated with the hydrogel compositions as defined in the present invention.

DETAILED DESCRIPTION OF THE INVENTION

Figure 1:
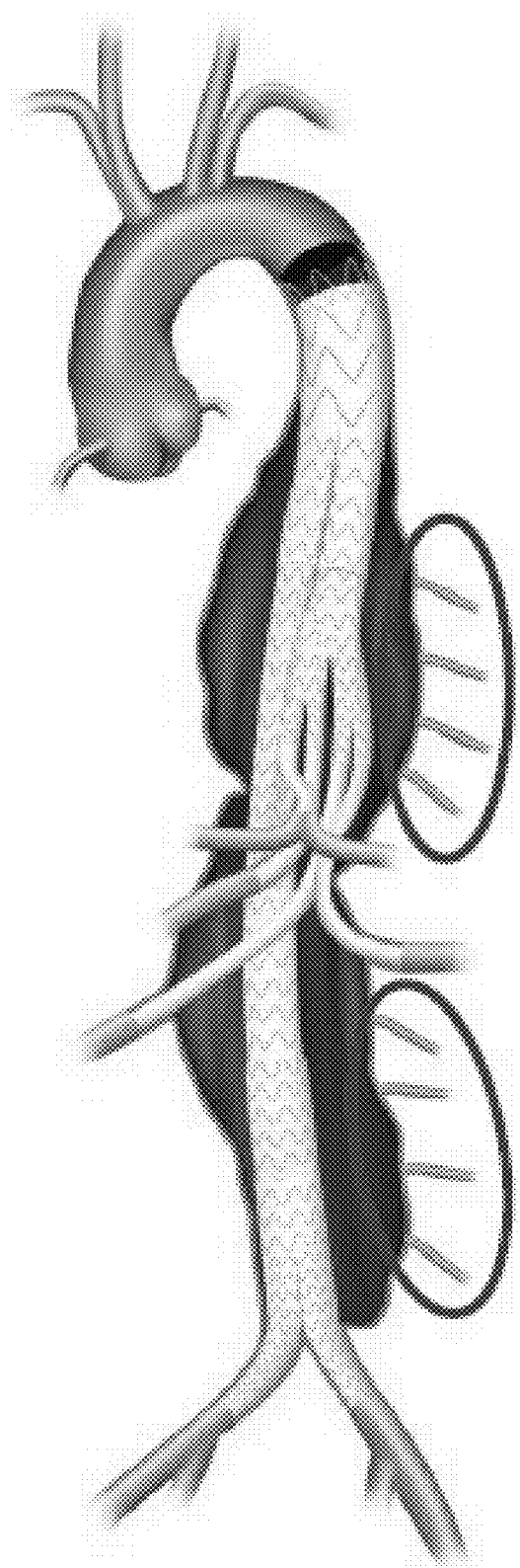
FIG. 1: Endovascular treatment of a thoracoabdominal aortic aneurysm (TAAA) with intercostal and lumbar arteries cut off from the blood supply.

In a first aspect, the present invention relates to an endovascular stent graft comprising an area having one or more through holes coated at least partially with a hydrogel capable of retarded reduction of the diameter of or retarded occlusion of said through holes by swelling upon implantation in a subject. The area having one or more through holes may be a porous membrane such as a textile porous membrane. As an example, the textile porous membrane is a warp knitted textile mesh structure.

The expressions "retarded reduction of the diameter of said through holes" and "retarded occlusion of said through holes" refer to a gradual occlusion of said through holes over the course of 1 to 4 weeks, preferably 1 to 3 weeks, more preferably about 2 weeks.

In one embodiment of the present invention the porous membrane is impregnated with at least one agent, selected from the group consisting of chemokines, growth factors, pharmaceuticals, co-factors, and functional micro- or nanoparticles.

The swellable hydrogel with a retardation profile is preferably a composition, comprising a polymer including a three-dimensional network of crosslinked polymer chains, wherein the main chains of said three-dimensional network are composed of poly(ethylene glycol) methyl ether methacrylate (PEGMEMA) polymer chains having the general formula (I)

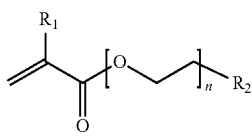
(I)

wherein $R_1$ is H or a linear or branched, substituted or unsubstituted alkyl group; $R_2$ is a linear or branched, substituted or unsubstituted alkyl group or a functional group, e.g. a hydroxyl group; and n is an integer from about 6 to about 45; and said main chains are crosslinked by at least an acrylate-based crosslinker comprising an internal disulfide moiety ("substantially degradable crosslinker").

Polymers (monomers) presenting alkyl-residues ($R_1$ is alkyl) in the polymer backbone form more flexible and sturdy hydrogels and thus are preferred. Also polymers in the range of 300-950 Mn provide more suitable results regarding the swelling and flexibility of the gels. In a preferred embodiment of the present invention, $R_1$ in formula (I) is methyl.

In preferred embodiments, the main chains of the three-dimensional network of crosslinked polymer chains comprised in the hydrogel compositions of the present invention are crosslinked not only by the above acrylate-based crosslinker comprising an internal disulfide moiety ("substantially degradable crosslinker"), but are additionally crosslinked by a (substantially stable or substantially non-degradable) crosslinker such as poly(ethylene glycol) diacrylate (PEGDA) crosslinker of the general formula (II)

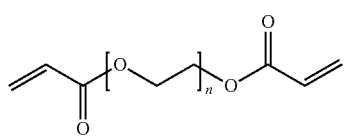
(II)

wherein n is an integer of from about 16 to about 400.

In particular, the main chains of the three-dimensional network may be crosslinked by
(i) said acrylate-based crosslinker comprising an internal disulfide moiety, and
(ii) said poly(ethylene glycol) diacrylate (PEGDA) crosslinker of the general formula (II).

The acrylate-based crosslinker comprising an internal disulfide moiety ("substantially degradable crosslinker") may have the following formula (III):

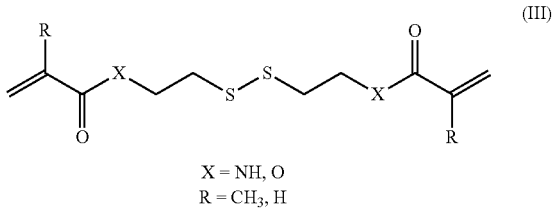
(III)

X = NH, O
R = CH₃, H

In the above formula (III), X is selected from NH and O; and R is selected from $CH_3$ and H.

In a preferred embodiment, the acrylate-based crosslinker comprising an internal disulfide moiety has the following formula (IV):

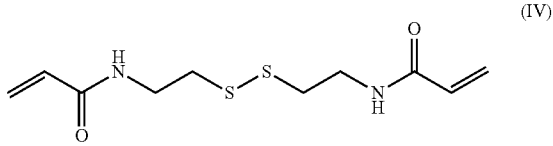 [SMILES: C=CC(=O)NCCSSCCNC(=O)C=C]
(IV)

In another preferred embodiment, the acrylate-based crosslinker comprising an internal disulfide moiety is Bis (2-methacryloyl)oxyethyl disulfide (DSDMA) according to the following formula (V):

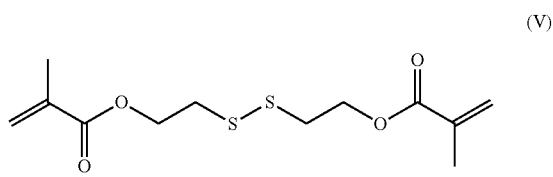 [SMILES: C=C(C)C(=O)OCCSSCCOC(=O)C(=C)C]
(V)

The acrylate-based crosslinker comprising an internal disulfide moiety may be present in an amount of at least about 10 mol-%, based on the hydrogel composition.

In specific embodiments of the present invention, the hydrogel composition in the endovascular stent graft of the present invention may further comprise at least one agent, selected from the group consisting of chemokines, growth factors, pharmaceuticals, co-factors, and functional micro- or nanoparticles.

The degradation profile focused in this invention implementing the degradation and recombination of disulfide and thiol groups was inter alia chosen due to the availability of an oxidizing agent Glutathione in the blood and possible supplementary addition of Glutathione by intravenous injection treatment. Also the possible recombination of thiols due to swelling of the gel is sought to increase the strength of the degrading hydrogel.

In preferred embodiments, the hydrogel compositions of the present invention comprise said acrylate-based crosslinker containing an internal disulfide moiety, e.g. DSDMA as defined above, in an amount of at least about 10 mol-%, based on the hydrogel composition.

In the examples, results were received using 3 mol % non-degradable crosslinker PEGDA as reference system. To test the degradation availability, hydrogels containing 3 mol %, 10 mol % and 20 mol % degradable crosslinker were analyzed.

Also a hydrogel composition of 1 mol % non-degradable PEGDA crosslinker and 2 mol % degradable DSDMA crosslinker was tested.

In specific embodiments of the present invention, both of the hydrogel compositions and the porous membranes can simultaneously comprise at least one agent, selected from the group consisting of chemokines, growth factors, pharmaceuticals, co-factors, and functional micro- or nanoparticles.

Methods for the actual generation of the hydrogel compositions of the present invention are not particularly limited and are known in the art. They include the use of polymerization initiators known in the art, such as e.g. 2,2'-Azobis (2-methylpropionamidine) dihydrochloride (AMPA), and the respective application of UV light, e.g. of 365 nm UV light in the case of AMPA.

Figure 2:
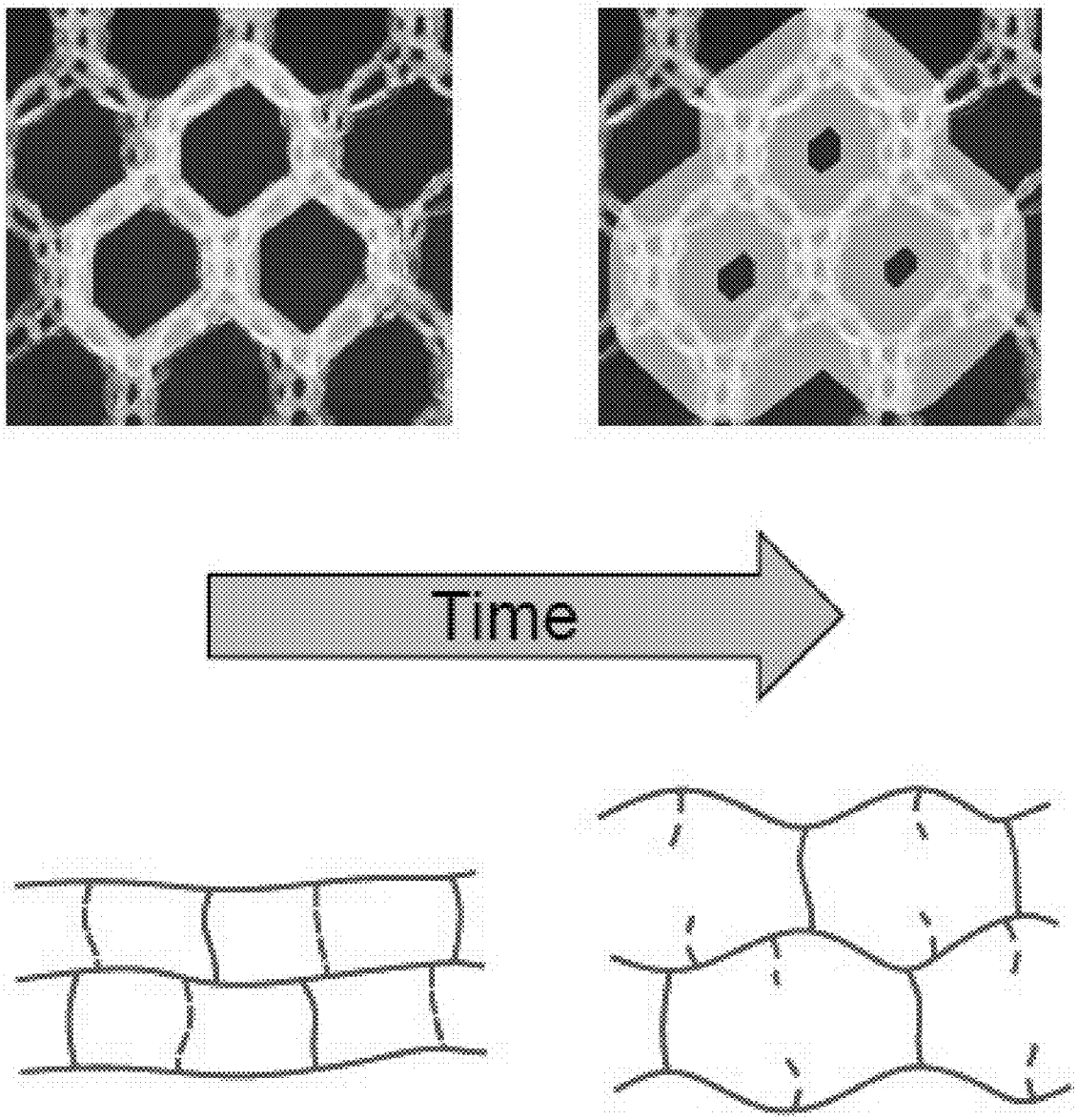
FIG. 2: Schematic demonstration of the controlled occluding textile hydrogel composite membrane of the present invention.
Figure 3:
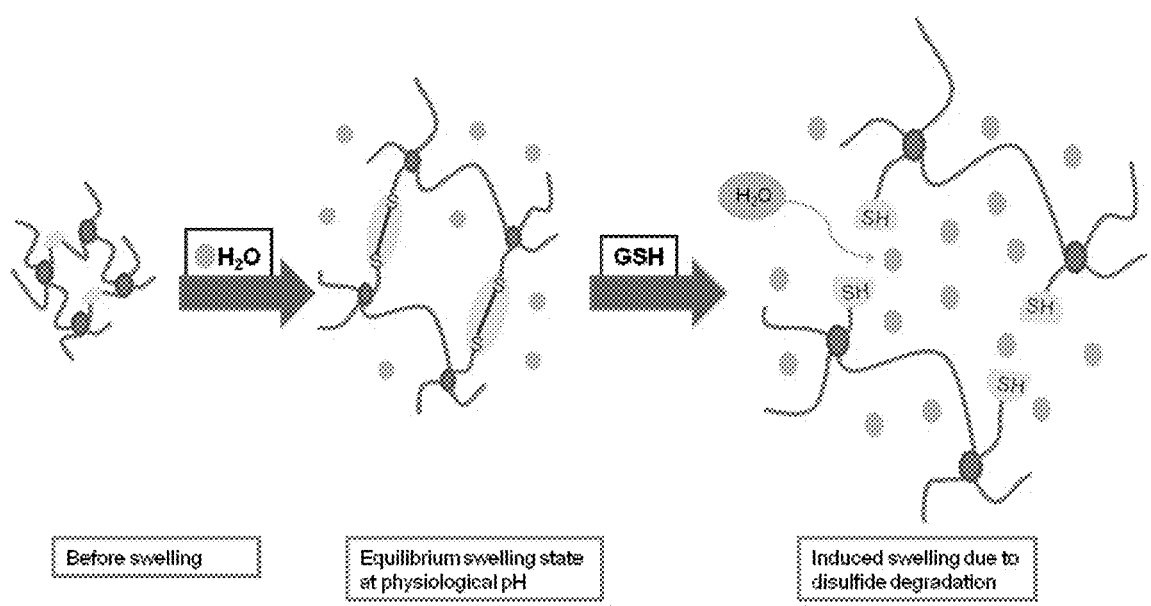
FIG. 3: Scheme of intended swelling profile of the hydrogel in PBS buffer pH 7.4 due to natural water uptake and further Glutathione induced swelling capability by disulfide oxidation of the crosslinker.

The hydrogel compositions of the present invention advantageously have the capability of swelling upon contact with blood in a retarded manner. In particular, said hydrogel compositions comprise a crosslinker that is degradable and optionally an additional crosslinker that is stable upon contact with blood or blood components. Specifically, glutathione contained in blood (typically in concentrations of about 1 mM) triggers the disruption of the acrylate-based crosslinker comprising an internal disulfide moiety, thus increasing the swelling capacity of the hydrogel composition (FIGS. 2 and 3).

The hydrogel compositions of the present invention are further characterized by a very high biocompatibility and mechanical stability (e.g. permanently withstanding a blood pressure of up to 200 mmHg). Thus, the hydrogel compositions are suitable for a wide range of medical applications in the context of cardiac and/or vascular treatments and procedures. The inclusion of further agents as defined above into the hydrogel compositions of the present invention can facilitate e.g. the migration of cells into the hydrogel, resulting in the generation of lasting and stable extracellular matrix structures.

The porous membranes of the present invention can be a non-textile mesh structure. However, in preferred embodiments, the porous membrane is a textile porous membrane, preferably a knitted structure and most preferably a warp knitted textile mesh structure. In specific embodiments, said structure can be a flat or a tubular structure. Said structure may be composed of any lapping enabling to obtain a structure with defined porosity, wherein preferably it is a mesh structure and most preferably a net structure.

The pore geometry may be but is not restricted to e.g. round, rectangular, hexagonal or trapezoidal. The machine gauge (needles per inch) is preferably between E18 and E32, more preferably between E24 and E32. The stitch density in the production direction (course count) is preferably between 6 to 20 stitches per cm. The pore size is preferably between 0.1 to 5 mm, more preferably between 0.2 to 3 mm referring to the diameter. The pore size above is defined for the macroscopic pores between several stitches/loops. The porosity of the textile structure is preferably between 10 to 90%, more preferably at least 50%. The porosity is defined as the ration of pore area: total area of the textile.

The material used may be e.g. PET, PP or PVDF but is not limited to these. The yarns used to build the textile structure and contained herein may be both mono- and/or multifilament yarns, preferably multifilament yarns.

According to the present invention, the through holes such as the pores of the porous membranes of the present invention are coated with the hydrogel compositions of the present invention. Specifically, this can be a sheathing (or coating) of only the borders of the pores defining the same, or a sheathing (or coating) of the entire mesh structure. Methods for the generation of respective porous membranes and for the coating of said membranes with the hydrogel compositions of the present invention are not particularly limited and are known in the art.

Types of endovascular stent grafts of the present invention are not particularly limited and are known in the art. In the endovascular stent grafts of the present invention, the area having one or more through holes such as a porous membrane can be disposed in any suitable manner, e.g. in a punctual, areal, circumferential, or longitudinal manner, wherein a circumferential disposition is preferred.

In a further aspect, the present invention relates to a tubular shunt, e.g. a shunt used as a temporary Blalock-Taussig shunt, wherein the inner walls of said shunt are coated with a hydrogel composition of the present invention. Types of respective shunts are not particularly limited and are known in the art.

In yet a further aspect, the present invention relates to a method for the repair of an aneurysm in a subject ("patient"), preferably an aortic aneurysm, more preferably a thoracic or thoracoabdominal aortic aneurysm, comprising the step of implanting the endovascular stent graft of the present invention into the affected vascular region of the subject. In preferred embodiments of this aspect, the subject is a human subject.

In a final aspect, the present invention relates to a method for the prevention of ischemic neurological damage in a subject ("patient") that is to receive an endovascular stent graft for the treatment of an aneurysm, preferably an aortic aneurysm, more preferably a thoracic or thoracoabdominal aortic aneurysm, comprising the step of implanting an endovascular stent graft of the present invention into the affected vascular region of the subject to treat said aneurysm. In preferred embodiments of this aspect, the subject is a human subject.

Further, ischemic neurological damage in this respect is preferably ischemic damage of the spinal cord, more preferably paraplegia.

The aim of the scientific investigations underlying the present invention was the development of a textile hydrogel composite membrane as a functional unit of a stent graft, which occludes in a controlled time interval (FIG. 2). The resulting, continuously decreasing blood flow will stimulate the body to form essential collateral spinal cord supply during that time interval. Thus the balancing act of safe endovascular aneurysm repair and the previously unresolved problem of protection against spinal ischemia can be performed.

The occluding membranes of the present invention comprise e.g. a textile hydrogel composite. In accordance with the determined product requirements, a warp knitted structure was developed as textile membrane component. Important aspects of the structure are the mechanical properties and the lapping, as well as the resulting pore size and the pore size distribution. The warp knitted structure was adjusted in such a way that the pores are fully occluded after the swelling of the hydrogel. The hydrogel system was developed according to the required occlusion period (e.g. about 2 weeks). The hydrogel was synthesized with a biodegradable and a stable crosslinker, wherein the dissolution of the degradable crosslinker results in an increased swelling capacity. Finally, the textile mesh structure was coated with the hydrogel and incorporated into a stent graft. Triggered by components of human blood (e.g. glutathione), the biodegradable crosslinker dissolves, so the hydrogel swells under controlled conditions and ultimately seals the membrane.

The present invention will be further illustrated in the following examples without any limitation thereto.

EXAMPLES

Example 1

A textile membrane component consisting of a warp knitted mesh structure according to the present invention was generated. The lapping of the mesh structure was chosen according to the swelling ratio and the coating behavior of the hydrogel. Two double-bar Raschel machines of type DR 16 EEC/EAC (gauge E16 and E30) and type DJ 6/2 EL (gauge E24 and E32) from Karl Mayer Textilmaschinenfabrik GmbH, Germany, were available for producing the mesh structure.

Further, a hydrogel system consisting of a main chain (PEGMEMA), a stable crosslinker (PEGDA), and a degradable crosslinker (DSDMA) according to the present invention was generated. As soon as the hydrogel was exposed to an aqueous environment, it began to swell until an equilibrium state was reached (FIG. 3, middle panel). In this state, the composite membrane could be processed and used as functional stent graft component. Once the membrane was in contact with blood, the gluthatione present in blood initiated the degradation of the degradable crosslinker (FIG. 3, right panel).

Example 2

Figure 4:
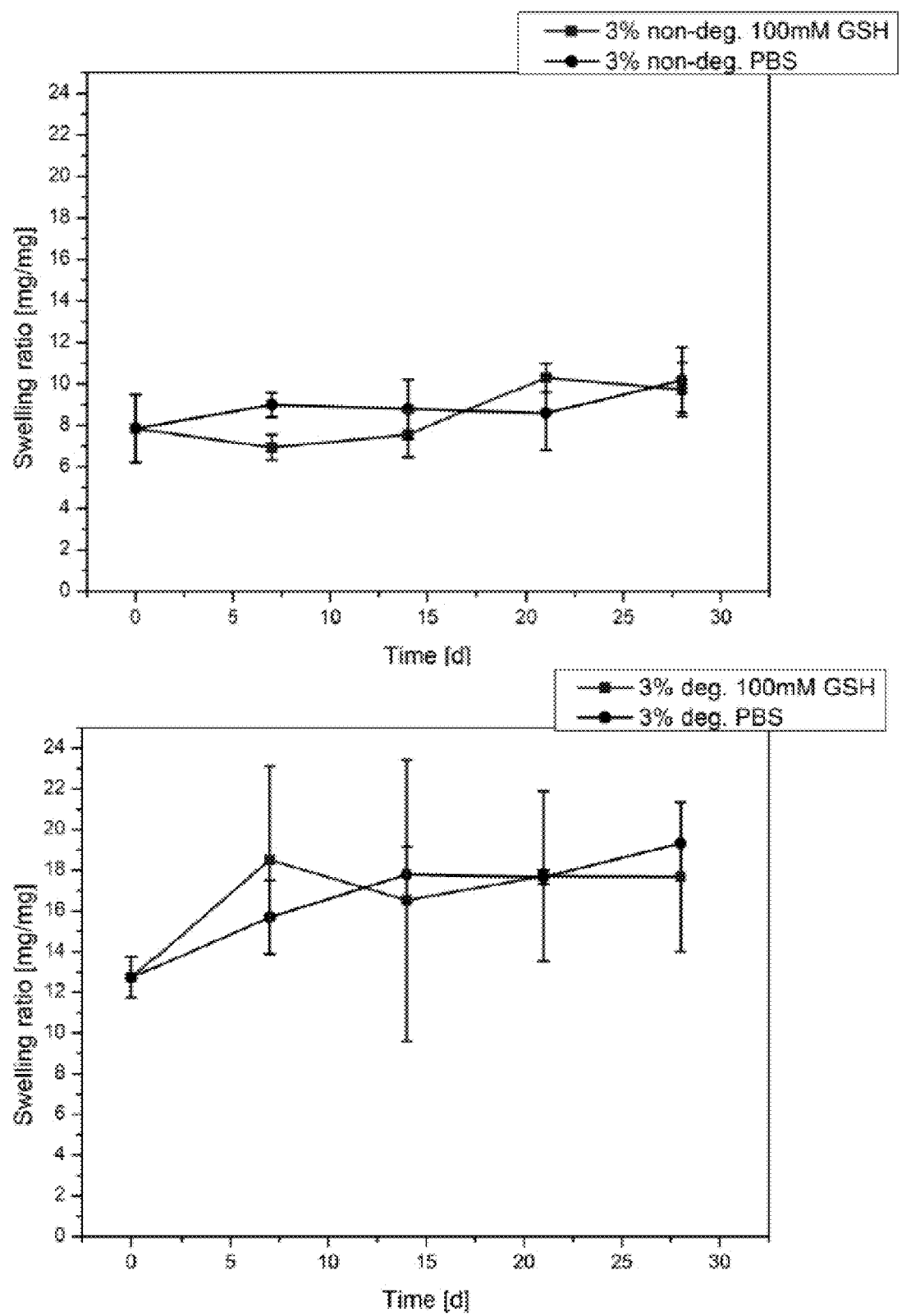
FIG. 4: Comparison of the swelling ratio over time using 100 mM Glutathione in PBS pH 7.4 buffer of 3 mol % non-degradable crosslinker (top, black) and degradable crosslinker (bottom, black). A reference sample tested in PBS buffer is presented respectively (blue).

For evaluation of the hydrogel systems of the present invention, various hydrogel compositions were investigated. The swelling behavior of the hydrogels was determined by mass determination and the mechanical properties by dynamic mechanical analysis. The samples were conditioned in phosphate buffered saline (PBS) solution with different amounts of gluthatione. The results show that even a hydrogel system without any stable crosslinker only degrades partially and shows sufficient mechanical stability after 21 days. Good results can also be achieved in terms of swelling behaviour (FIG. 4). The best results in terms of mechanical properties and swelling behaviour were achieved with a concentration of 20 mol % degradable crosslinker.

Synthesis of Hydrogels

All reactions tested using degradable crosslinker DSDMA as well as composition of both crosslinkers was carried out in a mixture of water and ethanol (2:3 ratio).

At first, AMPA was dissolved. Then crosslinker was added using a pipette and the vial was shaken until complete dissolution of crosslinker regarding PEGDA-700 as well as DSDMA Then the main chain macromolecule poly(ethylene glycol) methyl ether methacrylate was added, and the mixture was shaken well before activated by UV light (365 nm). UV light was supplied until complete polymerization was observed, which usually appeared after 1-4 hours. After successful gel formation, gels were carefully taken out of the reaction vial to purify gels of left over compounds by dialysis. Therefore the gels were placed into a 5 L bulk of water for 3 days. The water was changed 3 times per day carefully, to prevent the gels from rupturing.

During Dialysis it was observed that the gels swelled up to 70% of their previous size, increasing with increasing PEG length tested.

Degradation Performance

After purification, the gels were gently poured onto a PTFE slide and samples with a diameter of 6 mm and 10 mm were punched using a biopsy puncher (6 mm) and a pen cap (10 mm) and placed into a snap cap vial. Then PBS pH 7.4 was added and the samples were left aside for 1 day, to receive an equilibrium swelling state of the gels.

The punched samples were aligned in snap cap vials and 5-15 ml GSH in PBS buffer pH 7.4 was added. The buffer was prepared by dissolving a PBS table into 200 ml demineralized water. Then dry GSH was weight and accordingly dissolved in PBS buffer. To degrade, the samples were placed into a water bath at 37° C. or placed at room temperature and left for a period of 1-4 weeks. Samples that were tested at room temperature were set aside on the laboratory bench after preparation. Also references were prepared using only PBS pH 7.4 as environment for the gels.

Results

Figure 5:
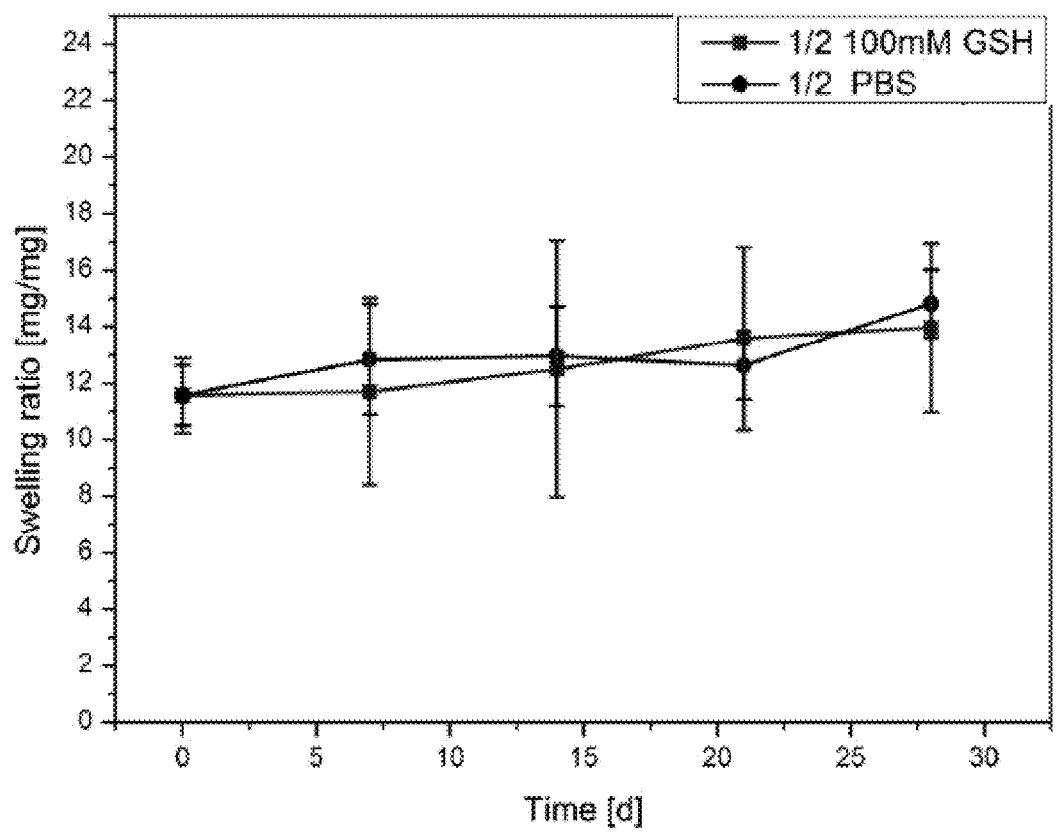
FIG. 5: Swelling ratio over time using 100 mM Glutathione in PBS pH 7.4 buffer of a hydrogel composition containing 1 mol % non-degradable crosslinker and 2 mol % degradable crosslinker (black). A reference sample tested in PBS buffer is presented respectively (blue).

It could be found, that by the comparison of the 3 mol % non-degradable crosslinker gel and the 3 mol % degradable crosslinker gel, the swelling increased due to degradation in 100 mM glutathione in PBS buffer solutions for the degradable gel (FIG. 4). Furthermore the composition gel containing 1 mol % non-degradable crosslinker and 2 mol % degradable crosslinker showed an increased swelling in 100 mM glutathione medium compared to gels in only PBS buffer (FIG. 5).

Figure 6:
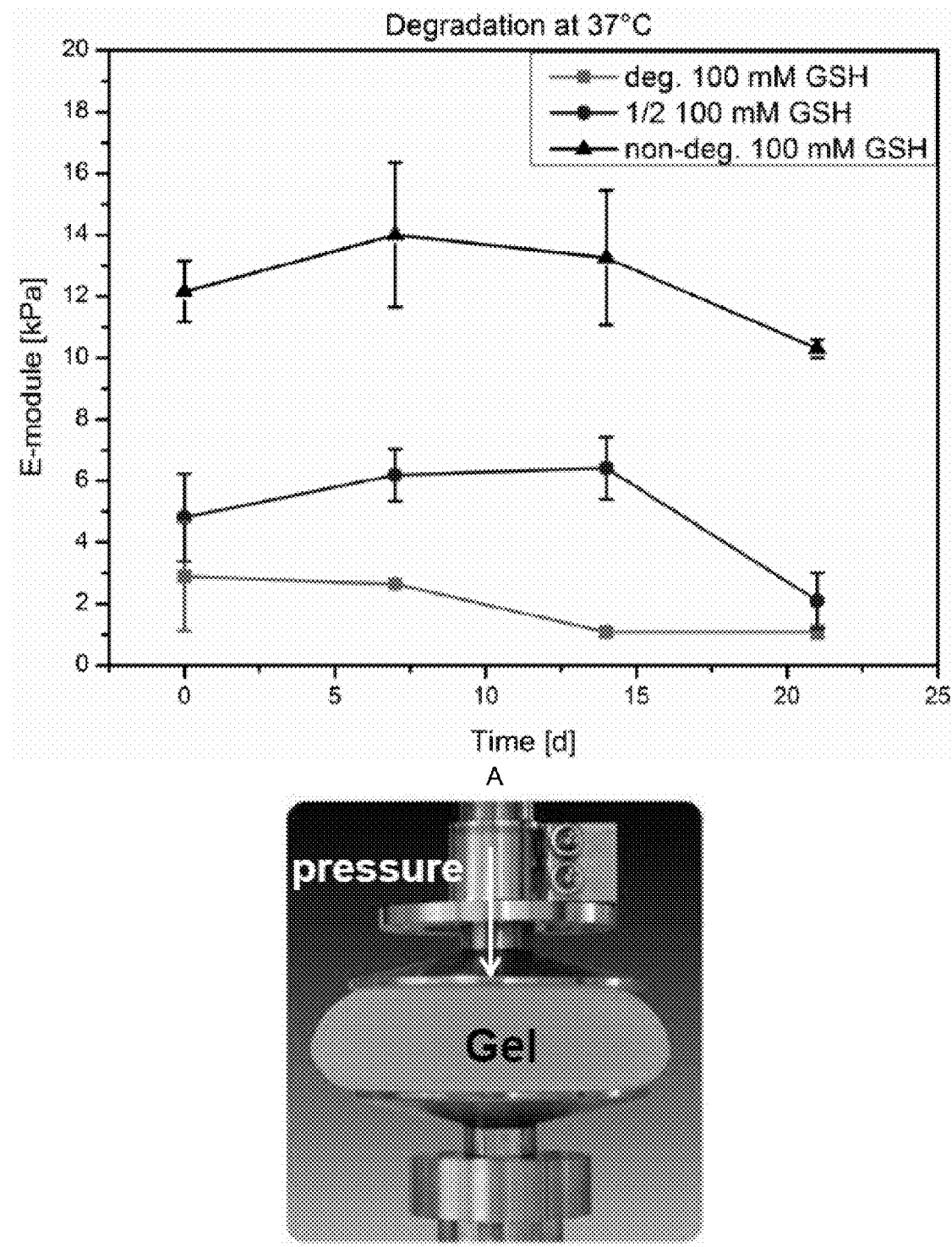
FIG. 6: E-module over time using 100 mM Glutathione in PBS pH 7.4 buffer of a degradable hydrogel containing 3 mol % degradable crosslinker (pink), 3 mol % non-degradable crosslinker (black) and a composition of 1 mol % non-degradable crosslinker and 2 mol % degradable crosslinker (blue).
Figure 7:
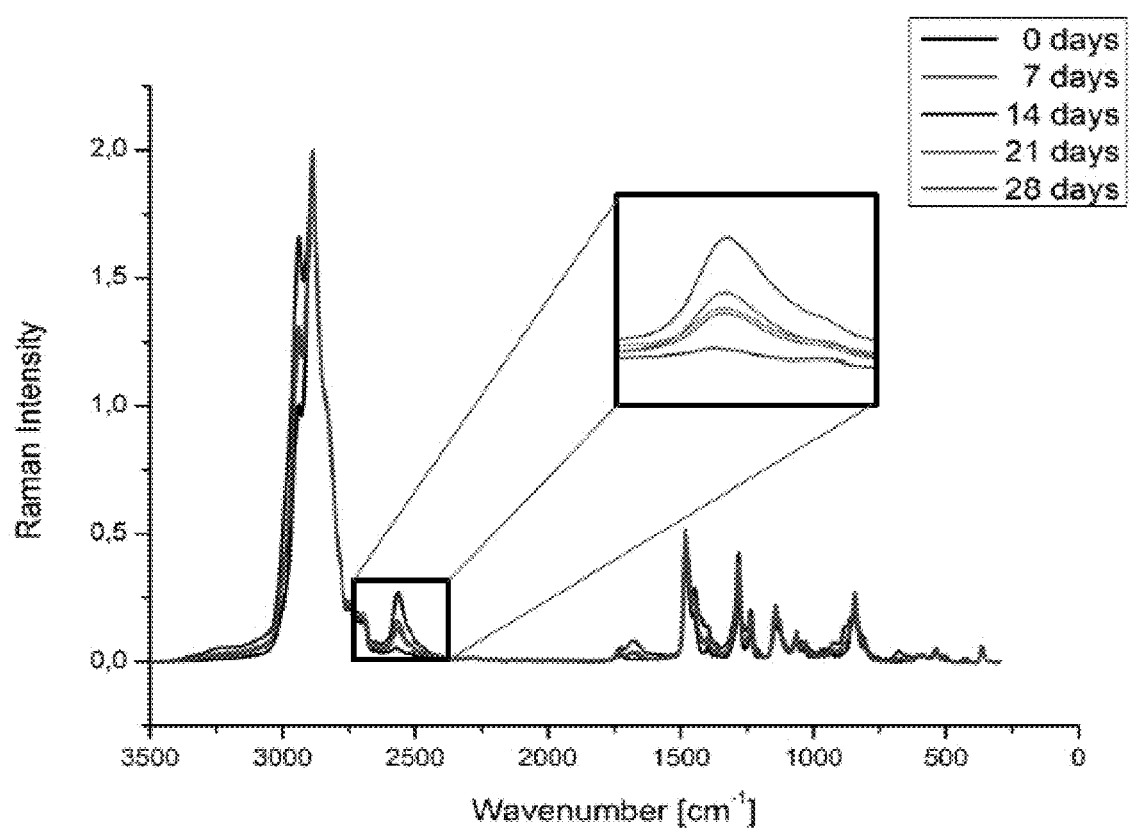
FIG. 7: Raman spectrum of the hydrogel containing 3 mol % degradable crosslinker over 28 days of degradation.

This could also be underlined by the observed decreasing toughness of the gels and decreasing E-module after degradation (FIG. 6) as well as the disulfide cleavage of the degradable crosslinker could be followed over time with Raman Spectroscopy (FIG. 7).

Figure 8:
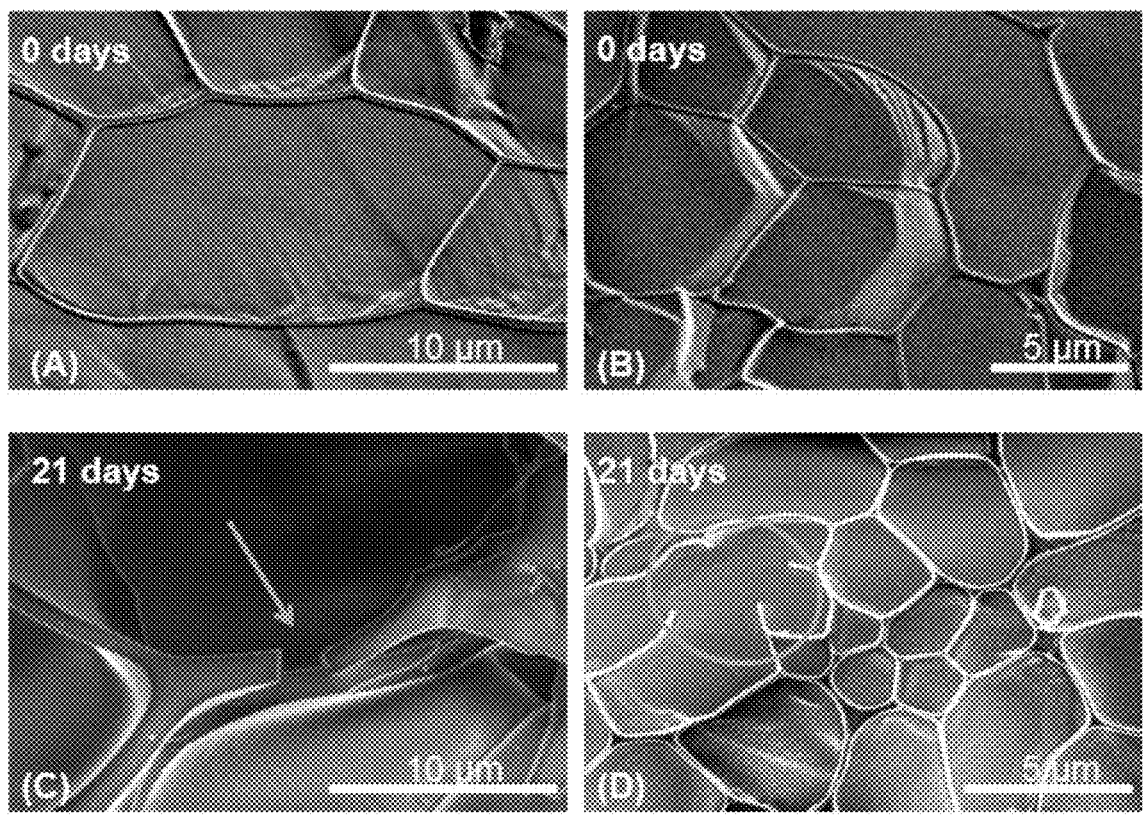
FIG. 8: Cryo-FESEM of hydrogels containing both crosslinkers after 21 days degradation.

The oxidation of the disulfide bond and therefore opening of the mesh sizes within the hydrogel could be shown using CryoFESEM (FIG. 8) as more cracks could be observed within the polymer network after degradation over 28 days in 100 mM Glutathione in PBS buffer at 37° C. and pH 7.4.

Figure 9:
FIG. 9: Photographs of different sizes of gel samples punched out of the synthesized and swollen hydrogel in PBS buffer.

The measurements were performed with individual samples of the same synthesized Hydrogel to avoid breaking of the gels during analysis. Therefore different sizes of gel samples were punched out of the synthesized and swollen hydrogel in PBS buffer (FIG. 9). Each analysis was performed with three same samples to guarantee the correct and reproducible outcome.

Figure 10:
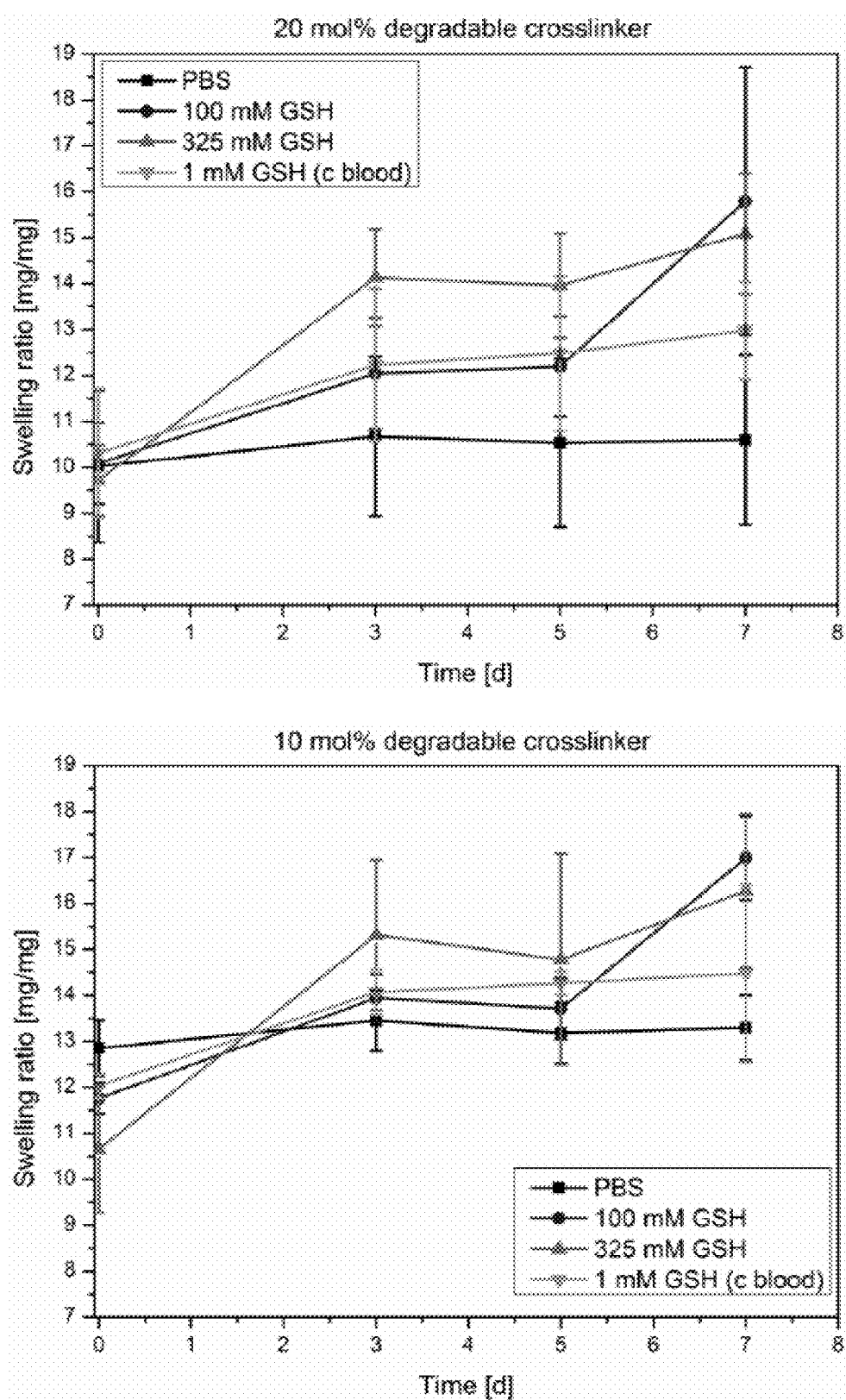
FIG. 10: Swelling ratio over 7 days using different (1 mM green, 100 mM blue, 325 mM pink) Glutathione in PBS pH 7.4 buffer of a degradable hydrogel containing 20 mol % degradable crosslinker (top) and 10 mol % degradable crosslinker (bottom). A reference sample tested in PBS buffer is presented respectively (black).

Furthermore to analysis degradability effects, two gels containing 10 mol % and 20 mol % degradable DSDMA crosslinker were analysis using different glutathione concentrations (1 mM, 100 mM, 325 mM) in PBS buffer at 37° C. over 7 days. Again an increased swelling was observed with all three tested Glutathione solutions (FIG. 10). This was observed for both tested gels (10 mol %, 20 mol %).

Figure 11:
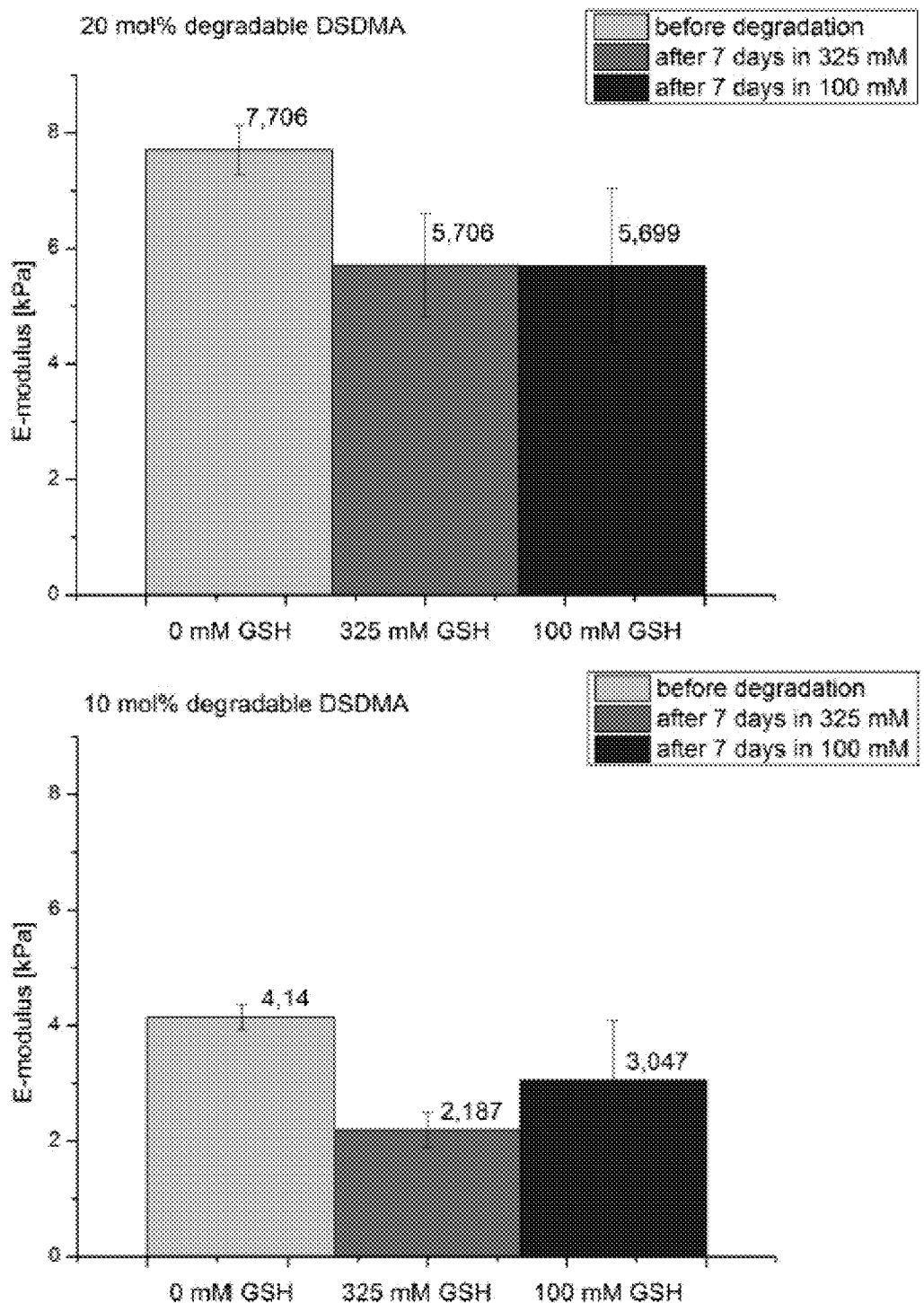
FIG. 11: E-module over 7 days using different (100 mM blue, 325 mM pink) Glutathione in PBS pH 7.4 buffer of a degradable hydrogel containing 20 mol % degradable crosslinker (top) and 10 mol % degradable crosslinker (bottom). A reference sample tested in PBS buffer is presented respectively (grey).
Figure 12:
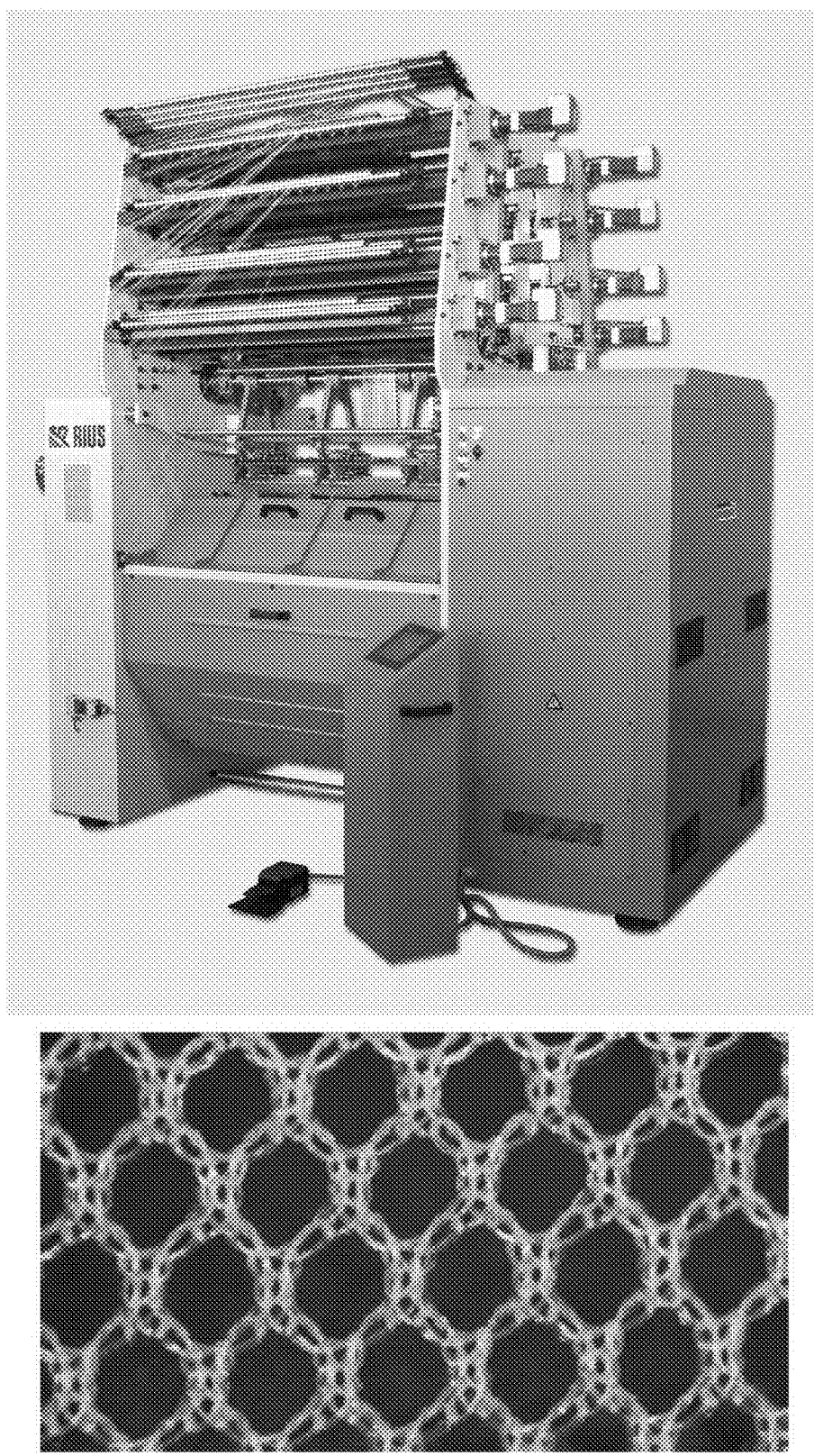
FIG. 12: Photographs of a warp knitting machine and a warp knitted textile mesh structure useful in connection with the present invention.

Continuing the 10 mol % and 20 mol % DSDMA containing gels were analyzed in regard of their E-module (FIG. 11), which also decreased due to the water uptake after degradation of the disulfide bond.

The invention claimed is:

1. An endovascular stent graft comprising an area having one or more through holes coated at least partially with a hydrogel capable of retarded reduction of the diameter of or retarded occlusion of said through holes by swelling upon implantation in a subject, wherein the retarded reduction or retarded occlusion occurs over a time course of one to four weeks.

2. The endovascular stent graft of claim 1, wherein said area having one or more through holes is a porous membrane.

3. The endovascular stent graft of claim 1, wherein said area having one or more through holes is a textile porous membrane.

4. The endovascular stent graft of claim 3, wherein said textile porous membrane is a warp knitted textile mesh structure.

5. The endovascular stent graft of claim 2, wherein said porous membrane is impregnated with at least one agent, selected from the group consisting of chemokines, growth factors, pharmaceuticals, co-factors, and functional micro- or nanoparticles.

6. The endovascular stent graft of claim 1, wherein said hydrogel is a composition, comprising a polymer including a three-dimensional network of crosslinked polymer chains, wherein the main chains of said three-dimensional network are composed of poly(ethylene glycol) methyl ether methacrylate (PEGMEMA) polymer chains having the general formula (I)

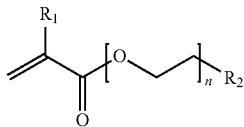

(I)

wherein $R_1$ is H or a linear or branched, substituted or unsubstituted alkyl group;

$R_2$ is a linear or branched, substituted or unsubstituted alkyl group or a functional group; and n is an integer of from about 6 to about 45; and said main chains are crosslinked by at least an acrylate-based crosslinker comprising an internal disulfide moiety.

7. The endovascular stent graft of claim 6, wherein said main chains are crosslinked by (i) said acrylate-based crosslinker comprising an internal disulfide moiety, and (ii) a poly(ethylene glycol) diacrylate (PEGDA) crosslinker of the general formula (II)

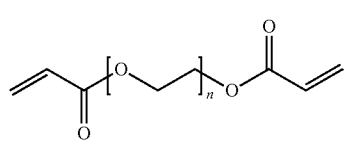

(II)

wherein n is an integer of from about 16 to about 400.

8. The endovascular stent graft of claim 6, wherein said acrylate-based crosslinker comprising an internal disulfide moiety has the following formula (III):

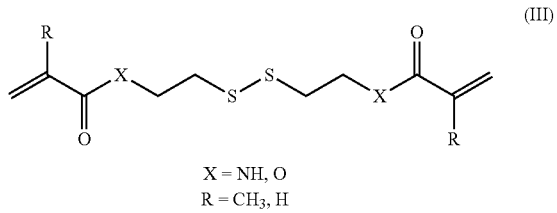

(III)

X = NH, O
R = CH₃, H wherein X is selected from NH and O; and R is selected from $CH_3$ and H.

9. The endovascular stent graft of claim 8, wherein said acrylate-based crosslinker comprising an internal disulfide moiety has the following formula (IV) or (V):

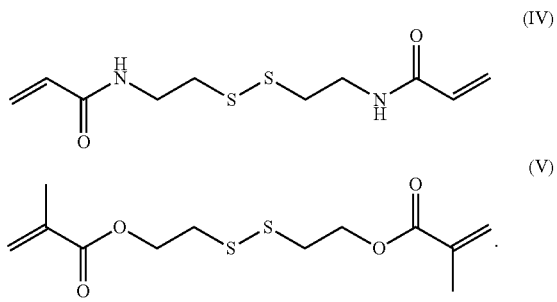

10. The endovascular stent graft of claim 6, wherein $R_1$ in formula (I) is methyl.

11. The endovascular stent graft of claim 6, wherein said acrylate-based crosslinker comprising an internal disulfide moiety is present in an amount of at least about 10 mol-%, based on the hydrogel composition.

12. The endovascular stent graft of claim 6, further comprising at least one agent, selected from the group consisting of chemokines, growth factors, pharmaceuticals, co-factors, and functional micro- or nanoparticles.

13. A method for the repair of an aneurysm in a subject, comprising the step of implanting the endovascular stent graft of claim 1 into the affected vascular region of the subject.

14. The method of claim 13, wherein the aneurysm is an aortic aneurysm.

15. The method of claim 14, wherein the aortic aneurysm is a thoracic or thoracoabdominal aortic aneurysm.

16. A method for the prevention of ischemic neurological damage in a subject that is to receive an endovascular stent graft for the treatment of an aneurysm, comprising the step of implanting the endovascular stent graft of claim 1 into the affected vascular region of the subject to treat said aneurysm.

17. The method of claim 16, wherein the aneurysm is an aortic aneurysm.

18. The method of claim 17, wherein the aortic aneurysm is a thoracic or thoracoabdominal aortic aneurysm.

19. The method of claim 16, wherein the ischemic neurological damage is ischemic damage of the spinal cord.

20. The method of claim 19, wherein the ischemic damage of the spinal cord is paraplegia.

21. A tubular shunt, wherein the inner walls of said shunt are coated at least partially with hydrogel capable of retarded swelling upon implantation in a subject and thereby reducing the diameter of said tubular shunt or closing said tubular shunt, wherein the retarded swelling occurs over a time course of one to four weeks.

22. The tubular shunt of claim 21, wherein said shunt is a temporary Blalock-Taussig shunt.

23. An endovascular stent graft comprising an area having one or more through holes coated at least partially with a hydrogel capable of retarded reduction of the diameter of or retarded occlusion of said through holes by swelling upon implantation in a subject wherein said hydrogel comprises a polymer including a three-dimensional network of cross-linked polymer chains comprised of poly(ethylene glycol) methyl ether methacrylate (PEGMEMA) polymer chains having the general formula (I)

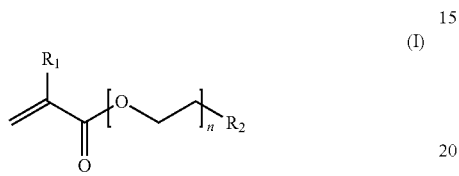

(I)

wherein $R_1$ is H or a linear or branched, substituted or unsubstituted alkyl group;

$R_2$ is a linear or branched, substituted or unsubstituted alkyl group or a functional group; and n is an integer of from about 6 to about 45; and said PEGMEMA polymer chains are crosslinked by at least an acrylate-based crosslinker comprising an internal disulfide moiety.

* * * * *